US007638682B2

(12) United States Patent
St. Martin et al.

(10) Patent No.: US 7,638,682 B2
(45) Date of Patent: Dec. 29, 2009

(54) SOYBEAN CULTIVAR HFPR-5

(75) Inventors: Steven K. St. Martin, Columbus, OH (US); Anne Dorrance, Wooster, OH (US); Ron J. Fioritto, Wooster, OH (US); Sue Ann Berry, Wooster, OH (US); Scott McIntyre, Wooster, OH (US); Marcia Feller, Nevada, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 184 days.

(21) Appl. No.: 11/952,525

(22) Filed: Dec. 7, 2007

(65) Prior Publication Data

US 2009/0151014 A1 Jun. 11, 2009

(51) Int. Cl.
*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl. .................... 800/312; 800/260; 800/278; 800/279; 800/286; 800/298; 800/300; 800/301; 800/302; 435/415; 435/430

(58) Field of Classification Search .............. None
See application file for complete search history.

(56) References Cited

U.S. PATENT DOCUMENTS

| | | |
|---|---|---|
| 5,491,081 A | 2/1996 | Webb |
| 6,162,967 A | 12/2000 | Webb |
| 6,538,175 B1 | 3/2003 | Webb |
| 7,041,880 B2 * | 5/2006 | Eby .................... 800/312 |
| 7,271,324 B2 | 9/2007 | Eby |
| 7,271,325 B1 | 9/2007 | Threlkeld et al. |
| 7,288,386 B2 | 10/2007 | Lightfoot et al. |
| 7,381,862 B2 | 6/2008 | St. Martin et al. |
| 7,435,873 B2 | 10/2008 | St. Martin et al. |
| 2006/0041955 A1 | 2/2006 | Godwin et al. |
| 2008/0127361 A1 | 5/2008 | St. Martin et al. |

FOREIGN PATENT DOCUMENTS

| | | |
|---|---|---|
| WO | 03094601 A1 | 11/2003 |
| WO | 05079380 A2 | 9/2005 |

OTHER PUBLICATIONS

Abney et al., New races of Phytophthora sojae with Rps1-d virulence, Plant Dis., vol. 81, No. 6, pp. 653-655, Jun. 1997.
Anderson et al., Inheritance and linkage of the Rps7 gene for resistance to Phytophthora rot of soybean, Plant Dis., vol. 76, No. 9, pp. 958-959, Sep. 1992.
Athow et al., A new major gene for resistance to Phytophthora megasperma var. sojae in soybean, Phytopathology, vol. 70, No. 10, pp. 977-980, 1980.
Athow et al., Rps6, a major gene for resistance to Phytophthora megasperma f. sp. glycinea in soybean, Phytopathology, vol. 72, No. 12, pp. 1564-1567, 1982.
Bernard et al., Inheritance of resistance to Phytophthora root and stem rot in soybean, Agron. J., 49:391, 1957.
Briggs et al., Introduction to Plant Breeding, Reinhold Publication Corp., New York, NY 1967.
Burnham et al., A new locus in soybean for resistance to Phytophthora sojae, Phytopathology, vol. 92, No. 6 (supplement), pp. S10-S11, Jul. 2002.
Burnham et al., Genetic Diversity Patterns among Phytophthora Resistant Soybean Plant Introductions Based on SSR Markers, Crop Sci., vol. 42, No. 2, pp. 338-343, Mar.-Apr. 2002.
Burnham et al., Quantitative trait loci for partial resistance to Phytophthora sojae in soybeans, Crop Sci., vol. 92, No. 6 (supplement), p. S11, 2002.
Burnham et al., Rps8, A New Locus in Soybean Resistance to Phytophthora sojae, Crop Sci. vol. 43, No. 1, pp. 101-105, Jan.-Feb. 2003.
Buzzell et al., Another major gene for resistance to Phytophthora megasperma var. sojae in soybeans, Soybean Genet., Newsl. 8:30-33, 1981.
Concibido et al., Genome mapping of soybean cyst nematode resistance genes in 'Peking', PI 90763, and PI 88788 using DNA markers, Crop Sci., vol. 37, No. 1, pp. 258-264, Jan.-Feb. 1997.
Cregan et al.. An integrated genetic linkage map of the soybean genome, Crop Sci., vol. 39, No. 5, pp. 1464-1490, Sep.-Oct. 1999.
Demirbas et al., Simple sequence repeat markers linked to the soybean Rps genes for Phytophthora resistance, Crop Sci., vol. 41, No. 4, pp. 1220-1227, Jul.-Aug. 2001.
Diers et al., Mapping Phytophthora Resistance Loci in Soybean with Restriction Fragment Length Polymorphism Markers, Crop Sci., vol. 32, No. 2, pp. 377-383, Mar.-Apr. 1992.
Dorrance et al., New Sources of Resistance to Phytophthora sojae in the Soybean Plant Introductions, Plant Dis., vol. 84, No. 12, pp. 1303-1308, Dec. 2000.

(Continued)

*Primary Examiner*—Stuart F. Baum
(74) *Attorney, Agent, or Firm*—Calfee, Halter & Griswold LLP

(57) ABSTRACT

A soybean cultivar designated HFPR-5 is disclosed. The invention relates to the seeds of soybean cultivar HFPR-5, to the plants of soybean HFPR-5, to plant parts of soybean cultivar HFPR-5 and to methods for producing a soybean plant produced by crossing soybean cultivar HFPR-5 with itself or with another soybean variety. The invention also relates to methods for producing a soybean plant containing in its genetic material one or more transgenes and to the transgenic soybean plants and plant parts produced by those methods. This invention also relates to soybean cultivars or breeding cultivars and plant parts derived from soybean variety HFPR-5, to methods for producing other soybean cultivars, lines or plant parts derived from soybean cultivar HFPR-5 and to the soybean plants, varieties, and their parts derived from use of those methods. The invention further relates to hybrid soybean seeds, plants and plant parts produced by crossing the cultivar HFPR-5 with another soybean cultivar.

25 Claims, No Drawings

OTHER PUBLICATIONS

Dorrance et al., Pathogenic diversity of Phytophthora sojae in Ohio soybean fields, Plant Dis., vol. 87, No. 2, pp. 139-146, Feb. 2003.

Dorrance et al., Reactions of Soybean Plant Introductions (PI273483 to PI427107) Following Inoculation with Phytophthora sojae, Ohio Agricultural Research and Development Center, Research Bulletin 1193, Jun. 2001.

Erwin et al., eds., Phytophthora, 1983, General resistance mechanisms against P sojae include structural features of the host, preformed chemical inhibitors, induced structural barriers, hypersensitive reactions and phytoalexins.

Gordon et al., Genetic Analysis of Soybean Plant Introductions with Resistance to Phytophthora sojae, 2007, The American Phytopathological Society, pp. 106-112.

Gordon et al., Rps8 Maps to a Resistance Gene Rich Region on Soybean Molecular Linkage Group F, Crop. Sci., vol. 46, No. 1, pp. 168-173, Jan.-Feb. 2006.

Hegstad et al., Identifying resistance to Phytophthora sojae in selected soybean accessions using RFLP techniques, Crop Sci., vol. 38, No. 1, pp. 50-55, Jan.-Feb. 1998.

Kaitany et al., Virulence composition of Phytophthora sojae in Michigan, Plant Dis., vol. 85, No. 10, pp. 1103-1106, Oct. 2001.

Kilen et al., Inheritance of a second major gene for resistance to Phytophthora root rot in soybeans, Crop Sci., vol. 14, No. 2, pp. 260-262, Mar.-Apr. 1974.

Kurle et al., Changing composition of Phytophthora sojae races in Minnesota soils, Phytopathology 91:S51, 2001.

Lande et al., Efficiency of Marker-Assisted Selection in the Improvement of Quantitative Trains, Genetics, 124:743-756, Mar. 1990.

Lee et al., Identification of quantitative trait loci for plant height, lodging, and maturity in a soybean population segregating for growth habit, Theor Appl Genet, (1996) 92:516-523.

Leitz et al., Races of Phytophthora sojae on Soybean in Illinois, Plant Dis., vol. 84, No. 4, p. 487, Apr. 2000.

Michelmore et al., Identification of markers linked to disease-resistance genes by bulked segregant analysis, Proc. Natl. Acad. Sci, USA, vol. 88, pp. 928-9832, Nov. 1991.

Mueller et al., Inheritance of resistance to four physiologic races of Phytophthora megasperms var. sojae, Phytopathology, 68:1318-1322, Sep. 1978.

Schmitthenner et al., Phytophthora sojae races in Ohio over a 10-year interval, Plant Dis., vol. 78, No. 3, pp. 269-276, Mar. 1994.

Schmitthenner et al., Problems and progress in control of Phytophthora root rot of soybean, Plant Dis., vol. 69, No. 4, pp. 362-368, Apr. 1985.

Shoemaker et al., Soybean Genomics, (2004), Soybeans: Improvement, Production, and Uses, 3rd ed., Agronomy Monograph No. 16, pp. 235-255.

Song et al., A new integrated genetic linkage map of the soybean, Theor Appl Genet, (2004) 109:122-128.

Soybean Growth and Development, 5 page printout from www.extension.umn.edu/distribution/cropsystemscomponents/5701a.html, Jun. 5, 2002.

St. Martin et al., Registration of 'Darby' Soybean; Registration of 'Kottman' Soybean; and Registration of HS93-4118 Soybean, Crop Sci., vol. 41, No. 2, pp. 590-591. Mar.-Apr. 2001.

Tijssen, Overview of Principles of Hybridization and the Strategy of Nucleic Acid Probe Assays, Laboratory Techniques in Biochemistry and Molecular Biology-Hybridization with Nucleic Acid Probes, Part I, Chapter 2, Elsevier, NY, 1993.

USDA, ARS, National Genetic Resource program. Germplasm Resource Information Network (GRIN [online database] National Germplasm Resources Laboratory, Beltsville, MD available: www.ars-grin.gov/cgi-bin/npgs/acc/display.pl?1300537 (Aug. 6, 2009).

U.S. Department of Agriculture, Technical Bulletin of 1987 reporting that PI 399073 was resistant to Phytophthora.

Van Ooijen et al., An RFLP linkage map of Lycopersicon peruvianum, Theor Appl Genet, (1994) 89:1007-1013.

Van Ooijen et al., JoinMap 3.0, Software for the calculation of genetic linkage maps, Plant Research International, Wageningen, The Netherlands, Oct. 2001.

Ward, The Interaction of Soya Beans with Phytophthora megasperma f.sp. glycinea: Pathogenicity, Biological Control of Soil-borne Plant Pathogens, edited by D. Homby, 1990, pp. 311-327.

Westman et al., The potential for cross-taxa simple-sequence repeat (SSR) amplification between Arabidopsis thaliana L. and crop brassicas, Theor Appl Genet, (1998) 96:272-281.

Wrather et al., Soybean disease loss estimates for the top ten soybean-producing countries in 1998, Can. J. Plant Pathol 23:115-121 (2001).

Yang et al., Races of Phytophthora sojae in Iowa soybean fields, Plant Dis., vol. 80, No. 12, pp. 1418-1420, Dec. 1996.

Notice of Allowance for U.S. Patent No. 7,381,862 mailed Apr. 1, 2005.

Amendment after Notice of Allowance for U.S. Patent No. 7,381,862 submitted Jun. 28, 2005.

Non-final Office Action for U.S. Patent No. 7,381,862 mailed Feb. 14, 2006.

Response to Non-final Office Action for U.S. Patent No. 7,381,862 submitted Jun. 14, 2006.

Final Office Action for U.S. Patent No. 7,381,862 mailed Aug. 24, 2006.

Response to Final Office Action for U.S. Patent No. 7,381,862 submitted Jan. 24, 2007.

Non-final Office Action for U.S. Patent No. 7,381,862 mailed Apr. 19, 2007.

Response to Non-final Office Action for U.S. Patent No. 7,381,862 submitted Aug. 20, 2007.

Final Office Action for U.S. Patent No. 7,381,862 mailed Oct. 30, 2007.

Examiner interview summary for U.S. Patent No. 7,381,862 mailed Dec. 11, 2007.

Response to Final Office Action for U.S. Patent No. 7,381,862 submitted Dec. 31, 2007.

Notice of Allowance for U.S. Patent No. 7,381,862 mailed Jan. 29, 2008.

Non-final Office Action for U.S. Patent No. 7,435,873 mailed Mar. 3, 2006.

Response to Non-final Office Action for U.S. Patent No. 7,435,873 submitted Sep. 5, 2006.

Non-final Office Action for U.S. Patent No. 7,435,873 mailed Nov. 14, 2006.

Response to Non-final Office Action for U.S. Patent No. 7,435,873 submitted Apr. 12, 2007.

Supplemental response to Non-final Office Action for U.S. Patent No. 7,435,873 submitted Jun. 15, 2007.

Notice of Allowance for U.S. Patent No. 7,435,873 mailed Sep. 10, 2007.

Amendment after Notice of Allowance for U.S. Patent No. 7,435,873 submitted May 28, 2008.

USPTO response to Amendment after Notice of Allowance for U.S. Patent No. 7,435,873 mailed Sep. 10, 2008.

\* cited by examiner

SOYBEAN CULTIVAR HFPR-5

GOVERNMENT RIGHTS

This invention was made, at least in part, with federal funding from the United States Department of Agriculture to Ohio Agricultural Research and Development Center (OARDC) in Hatch allocations. The United States Government has certain rights in this invention.

BACKGROUND

Soybean *Glycine max* (L) is an important oil seed crop and a valuable field crop. However, it began as a wild plant. This plant and a number of other plants have been developed into valuable agricultural crops through years of breeding and development. The pace of the development of soybeans, into an animal foodstuff and as an oil seed has dramatically increased in the last one hundred years. Planned programs of soybean breeding have increased the growth, yield and environmental hardiness of the soybean germplasm.

Due to the sexual reproduction traits of the soybean, the plant is basically self-pollinating. A self-pollinating plant permits pollen from one flower to be transferred to the same or another flower of the same plant. Cross-pollination occurs when the flower is pollinated with pollen from a different plant; however, soybean cross-pollination is a rare occurrence in nature.

Thus the growth and development of new soybean germplasm requires intervention by the breeder into the pollination of the soybean. The breeders' methods of intervening in the pollination depend on the type of trait that is being bred. Soybeans are developed for a number of different types of traits morphological (form and structure), phenotypical, or for traits like growth, day length, temperature requirements, tolerance to drought and heat, initiation date of floral or reproductive development, fatty acid contents, disease and insect resistance, herbicide resistance, yield, and generally better agronomic quality. The genetic complexity of the trait often drives the selection of the breeding method.

A devastating disease of soybean that occurs throughout the U.S. and the world is *Phytophthora* root and stem rot caused by *Phytophthora sojae*. Among soybean diseases, it is the second leading cause of yield loss in soybean in the United States. General resistance mechanisms against *P. sojae* include structural features of the host, preformed chemical inhibitors, induced structural barriers, hypersensitive reactions and phytoalexins. *Phytophthora* root and stem rot was first described in Ohio and shortly thereafter it was described in Indiana and North Carolina. The pathogen is now referred to as *Phytophthora sojae*.

Resistance to *Phytophthora* root and stem rot is a trait provided by multiple genes. Previously, thirteen resistance (Rps) genes at seven loci have been described; Rps1, Rps2, Rps3 Rps4, Rps5, Rps6, and Rps7. Recently, a new Rps resistance locus, Rps8, was described by the St, Martin et al. group in U.S. patent application Ser. No. 10/778,018, filed Feb. 12, 2004). Populations of *P. sojae* exist in many soybean production regions that cause disease on plants with many, if not all, of the Rps1-7 genes. However, so far, plants possessing Rps8 have shown resistance to all major *P. sojae* pathotypes, i.e. pathotypes virulence 1a, 1b, 1e, 1d, 1k, 2, 3a, 3b, 3c, 4, 5, 6 and 7. Because pathotypes of *P. sojae,* containing virulence genes to most of the Rps1-7 genes have already been found in various fields, it is desirable to introduce novel resistance loci or alleles, such as the Rps8 gene, into commercial soybean lines to protect against yield losses caused by *P. sojae.*

Due to the number of genes within each chromosome, millions of genetic combinations exist in the breeders' experimental soybean material. This genetic diversity is so vast that a breeder cannot produce the same two cultivars twice using the exact same starting parental material. Thus, developing a single variety of useful commercial soybean germplasm requires intensive research and development.

The development of new soybeans comes through breeding techniques, such as: recurrent selection, mass selection, backcrossing, single seed descent and multiple seed procedure. The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Additionally, marker assisted breeding allows more accurate movement of desired alleles or even specific genes or sections of chromosomes to within the germplasm that the breeder is developing. For example, RFLP, RAPD, AFLP, SSR, SNP, SCAR, isozymes, are all forms of markers that can be employed in breeding soybeans or in moving traits into soybean germplasm. Other breeding methods are known and are described in various plant breeding textbooks.

When a soybean variety is being employed to develop a new soybean variety or an improved variety, the selection methods include backcrossing, pedigree breeding, recurrent selection, modified selection and mass selection. The efficiency of the breeding procedure along with the goal of the breeding are the factors for determining which selection techniques are employed. A breeder continuously evaluates the success of the breeding program and therefore the efficiency of any breeding procedure. The success is usually measured by yield increase, commercial appeal and environmental adaptability of the developed germplasm.

The development of new soybean cultivars most often requires the development of hybrid crosses (some exceptions being initial development of mutants directly through the use of the mutating agent, certain materials introgressed by markers, or transformants made directly through transformation methods) and the selection of progeny therefrom. Hybrids can be achieved by manual manipulation of the sexual organs of the soybean or by the use of male sterility systems. Breeders often try to identify true hybrids by a readily identifiable trait or the visual differences between inbred and hybrid material. These heterozygous hybrids are then selected and repeatedly selfed and reselected to form new homozygous soybean lines.

Mass and recurrent selections can be used to improve populations of either self- or cross-pollinating crops. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued. Outcrossing to a number of different parents creates fairly heterozygous breeding populations.

Pedigree breeding is commonly used for the improvement of self-pollinating crops. Two parents that possess favorable, complementary traits are crossed to produce a F1 hybrid. The progeny of the F1 hybrid is selected and the best individual F2s are selected; this selection process is repeated in the F3 and F4 generations. The inbreeding is carried forward to an advances stage of inbreeding (e.g. F5-F7), where the best lines are selected and tested in the development stage for potential usefulness in a selected geographic area.

In backcross breeding a genetic allele is transferred into a desirable homozygous cultivar or inbred line which is the recurrent parent. The trait is in the donor parent and is tracked into the recurrent parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent method involves use of a segregating plant population for harvest of one seed per plant. Each seed sample is planted and the next generation is formed. When the F2 lines are advanced to the desired level of inbreeding, each plant will be derived from a different F2. The population will decline due to failure of some seeds to germinate or some plants to produce at least one seed. As a result, not all F2 plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max* L. Merr.) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994). {Note: The latest genetic map is found at the Soybase web site: http://soybase.org/.}

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which includes markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. Single locus or QTL mapping is the use of markers which are known to be closely linked to alleles that have measurable effects on a trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. For example, molecular markers are used in soybean breeding for selection of the trait of resistance to soybean cyst nematode, see U.S. Pat. No. 6,162, 967. The markers can also be used to select toward the genome of the recurrent parent and against the markers of the donor parent. This procedure attempts to minimize the amount of undesirable genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into soybean varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Allard, 1960; Simmonds, 1979; Sneep et al., 1979; Fehr, 1987).

New varieties must be tested thoroughly to compare their development with commercially available soybeans. This testing usually requires at least two years and up to six years of comparisons with other commercial soybeans. Varieties that lack the entire desirable package of traits can be used as parents in new populations for further selection or are simply discarded. The breeding and associated testing process can take up to 8 to 12 years prior to development of a new variety. Thousands of varietal lines are produced but only a few lines are selected in each step of the process.

The selected line or variety is evaluated for its growth, development, disease resistance, protein and oil composition, and yield. These traits of a soybean are a result of the variety's genetic potential interacting with its environment. All varieties have a maximum yield potential that is predetermined by its genetics. This hypothetical potential for yield is only obtained when the environmental conditions are perfect. Since perfect growth conditions do not exist, field experimentation is necessary to provide the environmental influence and to measure its effect on the development and yield of the soybean. The breeder attempts to select for good soybean yield potential under a number of different environmental conditions.

Selecting for good soybean yield potential in different environmental conditions is a process that requires planning based on the analysis of data in a number of seasons. Identification of the varieties carrying a superior combination of traits, which will give consistent yield potential, is a complex science. The desirable genotypic traits in the variety can be masked by other plant traits, unusual weather patterns, diseases, and insect damage. One widely employed method of identifying a superior plant with such genotypic traits is to observe its performance relative to commercial and experimental plants in replicated studies. These types of studies give more certainty to the genetic potential and usefulness of the plant across a number of environments.

In summary, the goal of the soybean plant breeder is to produce new and unique soybeans and progeny of the soybeans for farmers' commercial crop production. The development of new soybean cultivars requires the development and selection of soybean varieties, the crossing of these varieties and selection of superior hybrid crosses. Newer avenues for producing new and unique genetic alleles into soybeans, including introducing mutations or transgenes into the genetic material of the soybean, are now in practice in the breeding industry. These genetic alleles can alter pest resistance such as insect resistance, nematode resistance, herbicide resistance, or they can alter the plant's disease tolerance, or its fatty acid compositions, the amount of oil produced, and/or the amino acid compositions of the soybean plant or its seed.

The traits a breeder selects for when developing new soybeans are driven by the ultimate goal of the end user of the product. Thus if the goal of the end user is to resist a certain plant disease so overall more yield is achieved, then the breeder drives the introduction of genetic alleles and their selection based on disease resistant levels shown by the plant. On the other hand, if the goal is to produce a specific oil, with a high level of oleic acid and a lower level of linoleic acid, then the breeder may drive the selection of genetic alleles based on levels of fatty acids in the seed and accept some lesser yield potentials or other less desirable agronomic traits.

The new genetic alleles being introduced into soybeans are widening the potential uses and markets for the various products and by-products of the oil from the seed plants such as soybean. Soybean, *Glycine max* (L), is an important and valuable field crop. Thus, a continuing goal of soybean plant breeders is to develop stable, high yielding soybean cultivars that are agronomically sound.

SUMMARY

The invention generally relates to a new soybean cultivar designated HFPR-5.

One embodiment of the invention relates to seed of a soybean cultivar HFPR-5, a sample of the seed deposited under ATCC Accession No. PTA-8606.

Another embodiment relates to the plant from the soybean seed HFPR-5, or the plant parts.

In one embodiment, the plant has all of the physiological and morphological characteristics of a soybean plant produced by growing soybean seed HFPR-5.

In another embodiment, the plant is produced by growing the soybean seed HFPR-5.

In yet another embodiment, the plant is regenerated from tissue culture of regenerable cells of an HFPR-5 soybean plant, or parts thereof, wherein the HFPR-5 soybean plant is produced by growing soybean seed HFPR-5.

Included are plant parts selected from the following: leaf, pollen, stomatal cell, embryo, meristematic cell, root, root tip, anther, flower, ovule, seed, stem, pod, petal, cotyledons, hypocotyl, pistils or the cells thereof.

Another aspect relates to a tissue culture of regenerable cells of a soybean plant, or parts thereof, wherein the soybean plant is produced by growing the soybean seed HFPR-5, or parts thereof.

In some embodiments, the cells for the tissue culture are obtained from: the leaf, pollen, stomatal cell, embryo, meristematic cell, root, root tip, anther, flower, ovule, seed, stem, pod, petal, cotyledons, hypocotyl, pistils or the cells thereof.

Another embodiment covers a soybean plant regenerated from the tissue culture. In one example, the soybean plant regenerated from the tissue culture has all of the morphological and physiological characteristics of soybean cultivar HFPR-5.

Yet another embodiment encompasses pollen of a soybean plant grown from seed of a soybean cultivar HFPR-5, or parts thereof.

The present invention further relates to a method for producing a soybean seed or plant with the steps of crossing a first parent soybean plant with a second parent soybean plant to produce a progeny soybean plant or seed, wherein the first parent soybean is produced by growing soybean seed HFPR-5. The method can further include obtaining, harvesting, and/or growing progeny soybean seed obtained from the progeny soybean plant.

In embodiment aspect, the first and second soybean parents are different and the method produces a hybrid progeny soybean seed and plant.

In another embodiment, the progeny soybean plant or seed has all of the physiological and morphological characteristics of a soybean plant produced by growing soybean seed HFPR-5.

In another embodiment, second parent soybean plant is transgenic. In some examples, the transgenic second parent soybean plant contains genetic material selected from the following group: herbicide resistance, nematode resistance, insect resistance, resistance to disease, male sterility, or a combination thereof.

Also included are the progeny and hybrid progeny soybean seed, plant or parts thereof produced by any of the methods described above. Also included are the resultant seed or plant, or parts thereof, grown from the progeny or hybrid progeny seed, plant or parts thereof.

Yet another aspect of the invention covers a method for a breeding program using plant breeding techniques which employ the soybean plant HFPR-5 as plant breeding material and performing breeding by selection techniques, backcrossing, pedigree breeding, marker enhanced selection, mutation and transformation.

Also provided is a method of introducing a desired trait into soybean cultivar HFPR-5 wherein the method includes: a. crossing a HFPR-5 plant, produced by growing soybean designated HFPR-5, with a plant of another soybean cultivar that includes a desired trait to produce progeny plants; b. selecting one or more progeny plants that have the desired trait to produce selected progeny plants; c. crossing the selected progeny plants with the HFPR-5 plants to produce backcross progeny plants; d. selecting for backcross progeny plants that have the desired trait and all of the physiological and morphological characteristics of soybean cultivar HFPR-5; and e. repeating steps (c) and (d) three or more times in succession to produce selected fourth or higher backcross progeny plants that comprise the desired trait and all of the physiological and morphological characteristics of soybean cultivar HFPR-5.

The desired traits can be selected from the following group: male sterility, herbicide resistance, insect resistance, modified fatty acid metabolism, modified carbohydrate metabolism, or decreased phytate content, and resistance to bacterial disease, fungal disease or viral disease;

Definitions

In the description and tables that follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Cotyledon. A cotyledon is a type of seed leaf. The cotyledon contains the food storage tissues of the seed.

Embryo. The embryo is the small plant contained within a mature seed.

Height (ht.): Plant height is taken from the base of the soil to the topmost pod of the plant and is measured in inches.

Hilum. This refers to the scar left on the seed that marks the place where the seed was attached to the pod prior to the seed being harvested.

Hypocotyl. A hypocotyl is the portion of an embryo or seedling between the cotyledons and the root. Therefore, it can be considered a transition zone between shoot and root.

Lodging (lodg.): degree to which plants deviate from erect position at maturity. Rated from 1 (erect) to 5 (prostrate).

Maturity (mat): Number of days after August 31 for 95% of pods to reach their mature color.

Maturity rating (mat. rating): Rating of relative maturity of variety, based on maturity in relation to standard varieties and determined by linear interpolation. The term relative maturity is a numerical value that is assigned to a soybean variety based on comparisons with the maturity values of other varieties. The number preceding the decimal point in the maturity rating refers to the maturity group. The number following the decimal point refers to the relative earliness or lateness within each maturity group. For example, a 3.0 is an early group III variety, while a 3.9 is a late group III variety.

Maturity Group. This refers to an agreed-on industry division of groups of varieties based on zones in which they are adapted, primarily according to day length or latitude. They consist of very long day length varieties (Groups 000, 00, 0), and extend to very short day length varieties (Groups VII, VIII, IX, X).

Oil or oil percent. Soybean seeds contain a considerable amount of oil. Oil is measured by NIR spectrophotometry, and is reported on as percentage dry-weight basis.

Partial resistance: quantitative degree of resistance to a compatible isolate of *P. sojae* (i.e., an isolate that produces a susceptible reaction). Rated on a scale of 1 (excellent) to 9 (very poor).

Pod. This refers to the fruit of a soybean plant. It consists of the hull or shell (pericarp) and the soybean seeds.

Protein Percent. Soybean seeds contain a considerable amount of protein. Seed protein content is generally measured by NIR spectrophotometry and is reported as percentage of dry-weight basis.

Pubescence. This refers to a covering of very fine hairs closely arranged on the leaves, stems and pods of the soybean plant.

Quantitative Trait Loci (QTL,). Quantitative trait loci (QTL) refer to genetic loci that control to some degree numerically representable traits that are usually continuously distributed.

Rank: yield rank among tested entries.

Regeneration. Regeneration refers to the development of a plant from tissue culture.

Rps genes: major genes for resistance to *Phytophthora sojae*, determined by hypocotyl inoculation using standard *P. sojae* isolates. The most common genes are Rps1a, Rps1c, Rps1k, Rps3a and Rps8, a newly discovered *P. sojae* resistance gene.

Yield (Bushels/Acre). The yield in bushels/acre is the actual yield of the grain at harvest, adjusted to 13% moisture.

YieldXX: refers to yield at a particular location ('xx'); location codes are pc: Plain City, wc: Lakeview, we: South Charleston, nw, Hoytville, wo: Wooster.

Seed quality (sdqual): degree of wrinkling, defective seed coat, greenishness, mold, or other pigment. Rated from 1 (very good) to 5 (very poor).

Seed weight (sdwt.): weight in grams of 100 random seeds, adjusted to 13% moisture content.

Single Gene Converted (Conversion). Single gene converted (conversion) plants refers to plants which are developed by a plant breeding technique called backcrossing wherein essentially all of the desired morphological and physiological characteristics of a variety are recovered in addition to the single gene transferred into the variety via the backcrossing technique or via genetic engineering.

A transgene or transgenic plant refers to a plant that possess a gene or genes that have been transferred from a different species. Although DNA of another species can be integrated in a plant genome by natural processes, the term "transgenic plants" refers to plants created in a laboratory using recombinant DNA technology.

The present invention will be better understood by reference to the following examples which are offered by way of illustration not limitation.

DETAILED DESCRIPTION

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

According to the invention, there is provided a new soybean cultivar designated HFPR-5. This invention thus relates to the seeds of soybean cultivar HFPR-5, to the plants of soybean cultivar HFPR-5, and to methods for producing a soybean plant produced by crossing the soybean cultivar HFPR-5 with itself or another soybean cultivar, and the creation of variants by mutagenesis or transformation of soybean cultivar HFPR-5.

Accordingly, the invention encompasses soybean seed designated HFPR-5, a sample of which was deposited with the American Type Culture Collection (ATCC) on Aug. 17, 2007, under Accession No. PTA-8606.

Another embodiment relates to a soybean plant, or parts thereof, having all of the physiological and morphological characteristics of a plant of soybean cultivar HFPR-5 produced by growing soybean seed HFPR-5. In one example, such a soybean plant is produced by growing the soybean seed HFPR-5. In another example, such a soybean plant is regenerated from tissue culture of regenerable cells of a soybean cultivar HFPR-5 plant, or parts thereof.

Another embodiment relates to soybean plant parts, which include, but are not limited to: leaf, pollen, stomatal cell, embryo, meristematic cell, root, root tip, anther, flower, ovule, seed, stem, pod, petal, cotyledons, hypocotyl, pistils and the cells thereof.

In another aspect, the invention provides a tissue culture of regenerable cells of a soybean plant HFPR-5, or parts thereof. In one example, the tissue culture will be capable of regenerating plants having all the physiological and morphological characteristics of the HFPR-5 soybean plant, and of regenerating plants having substantially the same genotype as the HFPR-5 soybean plant. For example, regenerable cells in such tissue cultures may be obtained from: leaf, pollen, stomatal cell, embryo, protoplasts, meristematic cell, callus, root, root tip, anther, flower, ovule, seed, stem, pod, petal, cotyledons, hypocotyl, or pistils. Accordingly, the present invention also provides soybean plants regenerated from the tissue cultures of the invention.

This invention is also directed to methods for producing a soybean plant by crossing a first parent soybean plant with a second parent soybean plant to produce a progeny soybean plant or seed. In this method, at least the first parent soybean plant is the soybean plant from cultivar HFPR-5. Further, both first and second parent soybean plants may be from cultivar HFPR-5 Therefore, any breeding methods using soybean cultivar HFPR-5 are part of this invention. Example of such methods include, but are not limited to, selfing, backcrosses, hybrid breeding, and crosses to populations, and the like. Any plants produced using soybean cultivar HFPR-5 as at least one parent are within the scope of this invention.

For example, the soybean cultivar HFPR-5 can be used in crosses with other, different, soybean plants to produce first generation ($F_1$) soybean hybrid seeds and plants with superior characteristics.

In another example, both first and second parent soybean plants are from cultivar HFPR-5 and the progeny soybean has all of the physiological and morphological characteristics of a soybean plant produced by growing soybean seed HFPR-5.

In another example, the second parent soybean is transgenic. Such a transgenic plant can contain exogenous genetic material, including, but not limited to, herbicide resistance, nematode resistance, insect resistance, resistance to disease, male sterility or a combination of these. In some examples, the resistance to disease is through an oxalate oxidase encoding polynucleotide sequence or an oxalate decarboxylase encoding polynucleotide sequence.

In some example, such transgenic plants can be produced by introducing expression vectors into plant tissues using a direct gene transfer method, including, but not limited to, microprojectile-mediated delivery, DNA injection, electroporation or the like. For example, expression vectors can be introduced into plant tissues by using either microprojectile-mediated delivery with a biolistic device or by using *Agrobacterium*-mediated transformation. Provided herein are also transformant plants obtained with the protoplasm of the soybean plants.

Another aspect relates to single or multiple gene converted plants of soybean cultivar HFPR-5. The transferred gene(s) may be a dominant or recessive allele. In some examples, the transferred gene(s) will confer such traits as herbicide resistance, insect resistance, resistance for bacterial, fungal, or viral disease, male fertility, male sterility, enhanced nutritional quality, and industrial usage. The gene may be a naturally occurring soybean gene or a transgene introduced through genetic engineering techniques.

Yet another aspect relates to a method of introducing a desired trait into soybean cultivar HFPR-5, as well as the resultant transformed soybean plants. Such methods include:

a. crossing a HFPR-5 plant, produced by growing soybean designated HFPR-5, with a plant of another soybean cultivar that includes a desired trait to produce progeny plants. Such desired traits include: male sterility, herbicide resistance, insect resistance, modified fatty acid metabolism, modified carbohydrate metabolism, or decreased phytate content, and resistance to bacterial disease, fungal disease or viral disease;

b. selecting one or more progeny plants that have the desired trait to produce selected progeny plants;

c. crossing the selected progeny plants with the HFPR-5 plants to produce backcross progeny plants;

d. selecting for backcross progeny plants that have the desired trait and all of the physiological and morphological characteristics of soybean cultivar HFPR-5 (e.g. as listed in Table 5); and e. repeating steps (c) and (d) three or more times in succession to produce selected fourth or higher backcross progeny plants that comprise the desired trait and all of the physiological and morphological characteristics of soybean cultivar HFPR-5 (e.g. as listed in Table 5).

When the desired trait is herbicide resistance, the resistance can be conferred to an herbicide selected from the group consisting of imidazolinone, sulfonylurea, glyphosate, glufosinate, L-phosphinothricin, triazine and benzonitrile.

When the desired trait is insect resistance, the insect resistance can be conferred by a transgene encoding a *Bacillus thuringiensis* endotoxin.

When the desired trait is modified fatty acid metabolism, modified carbohydrate metabolism, or decreased phytate content, the desired trait can be conferred by a nucleic acid encoding a protein selected from the following group: phytase, fructosyltransferase, levansucrase, α-amylase, invertase and starch branching enzyme. Alternatively, the method can include transforming a plant with an antisense gene of stearyl-ACP desaturase.

Soybean Cultivar HFPR-5

Soybean cultivar HFPR-5 is a conventional (non-glyphosate resistant) line derived from Kottman by generations of backcrossing.

HFPR-5 was developed from a soybean germplasm, OX01-602, known to carry the novel Rps8 resistance gene. Plants carrying the Rps8 gene are resistant to *P. sojae* pathotypes vir1a, 1b, 1c, 1d, 1k, 2, 3a, 3b, 3c, 4, 5, 6 and 7. The development of OX01-602 (also referred to as HFX01-602) and the genetic localization of Rps8 are described in U.S. patent application "Identification of Soybeans Having Resistance to *Phytophthora Sojae*" to St. Martin et al., Ser. No. 10/778,018, filed Feb. 12, 2004, the entire contents of which are incorporated herein by reference. Homozygous Rps8 progeny of OX01-602 were deposited with the ATCC on May 9, 2003, under ATCC Accession No: PTA-5190. (See St. Martin, et al, U.S. patent application Ser. No. 10/436,376, Filed: May 12, 2003).

Soybean cultivar HFPR-5 is a BC3F$_2$-derived line from the backcross Kottman$^4$×(PI 399.073×Northrup King S19-90). The cross and backcrosses were made at Wooster with the objective of transferring the Rps8 gene for resistance to *P. sojae* into the Kottman background. Table 1 shows the breeding timeline. Multiple assays for response to *P. sojae* were conducted to ensure that HFPR-5 is homozygous for Rps8. (see Table 2). The *P. sojae* inoculation assays are described in Gordon et al. 2007, *Phytopathology* 97:106-112, the entire contents of which are incorporated herein by reference. Briefly, seeds were germinated in moist paper towels and placed in the dark at room temperature. After 7 days, a hypodermic syringe was used to inoculate the hypocotyls of each seedling with agar containing a 7-day old culture of *P. sojae*. Results of the inoculations of HFPR-5 with several *P. sojae* isolates are shown in Table 2. Each column is the *P. sojae* isolate designation, the reaction on the controls indicates the pathotype. The pathotype is based on the 90 to 100% kill of the controls. *P. sojae* R-1 has virulence for Rps7; R17 virulence for 1b, 1k, 2, 3a, 3b, 3c, 4, 5, 6, 7; R-25 virulence for 1a, 1b, 1c, 1k, 7; ss05NWBS16 (1a, 1b, 1k, 3c, 4, 6, 7); z30-2 (1a, 1b, 1k, 2, 3a, 5, 6, 7); 12z24oos4-2 (1a, 3a, 3c, 4, 6, 7, 8); 12z24 oos4-5 (1a,2,3c,4,5,6,7). (See Table 2).

Kottman, the recurrent parent is a commercial variety developed by OARDC (St. Martin et al., 2001. Crop Sci. 41:490-491). NK S19-90 is available from Northrup King Com., Stenton, Minn.

TABLE 1

Breeding Timetable

| | |
|---|---|
| First cross: | OXRSc198317 made by crossing PI 399073 with NK S19-90. |
| Second cross: | OXR99393 made by crossing OXRSc198317 with Kottman. |
| Third cross: | OX01-602 made by crossing Kottman with OXR99393. |
| Fourth cross: | GX01-03 made by crossing Kottman with OX01-602. |
| Fifth cross: | OX02-001 made by crossing Kottman with GX01-03. BC3F$_1$ plant grown. |
| First harvest: | BC3 F$_2$ plants grown and harvested individually. |
| Second harvest: | BC3F$_2$-derived lines increased in Puerto Rico and tested for reaction to *P. sojae*. Line HFPR-5, homozygous for Rps8, was among those retained. |
| First Field Test: | HFPR-5 tested for yield and agronomic traits at Columbus and Wooster, OH. Seed increased and purified at Wooster. |
| Second Field Test: | HFPR-5 seed increased at Croton, OH; inspected for uniformity and purity. Further tested to confirm reaction to *P. sojae*. Field tests conducted in Ohio and in USDA regional soybean tests. |
| Third Field Test: | Agronomic tests conducted in Ohio. |

TABLE 2

Reaction of soybean varieties to isolates of *Phytophthora sojae*,

| | *P. sojae* isolate | | | | | | | |
|---|---|---|---|---|---|---|---|---|
| | R-1 | R-17 | R-25 | ss05 NWBS16 | z30-2 | 04s1s1 12z24 oos4-2 | 04s1s1 12z24 oos4-5 | GENES |
| St. Martin Varieties | | | | | | | | |
| Wyandot | 0\15† | 15\15 | 0\20 | 0\18 | 19\20 | 20\20 | 20\20 | 3a |
| HFPR3 | 0\18 | 3\11 | 0\19 | 0\20 | 19\20 | 3\19 | 3\20 | 1k, 3a, 8 |
| HFPR4 | 0\20 | 1\16 | 0\20 | 1\20 | 20\20 | 2\20 | 2\18 | 1k, 3a, 8 |
| HFPR5 | 0\19 | 0\17 | 0\18 | 7\19 | 2\20 | 11\20 | 3\20 | seg 1k, 3a, 8 |
| HS1-3661 | 0\18 | 0\19 | 14\16 | 1\16 | 18\19 | 2\15 | 3\17 | 1k |
| HS1-3710 | 0\20 | 0\20 | 1\17 | 4\17 | 19\20 | 2\15 | 5\19 | 1k, 3a, 8 |
| Dennison | 0\15 | 9\16 | 1\19 | 0\20 | 19\20 | 9\19 | 11\20 | seg 1k, 3a |
| HS1-3886 | 0\17 | 1\16 | 20\20 | 2\20 | 0\20 | 3\20 | 4\20 | 1k |

TABLE 2-continued

Reaction of soybean varieties to isolates of *Phytophthora sojae*.

| | | | | *P. sojae* isolate | | | | |
|---|---|---|---|---|---|---|---|---|
| | R-1 | R-17 | R-25 | ss05 NWBS16 | z30-2 | 04s1s1 12z24 oos4-2 | 04s1s1 12z24 oos4-5 | GENES |
| Controls‡ | | | | | | | | |
| susceptible | 8\8 | 8\8 | 8\8 | 8\8 | 8\8 | 8\8 | 8\8 | |
| Rps1a | ¶ | 1\8 | 8\8 | 8\8 | 8\8 | 7\8 | 8\8 | |
| Rps1b | | 8\8 | 8\8 | 8\8 | 7\8 | | 1\8 | |
| Rps1c | | | 8\8 | | 1\8 | | | |
| Rps1d | | 3\8 | | | | | 1\8 | |
| Rps1k | | 1\8 | 8\8 | | 8\8 | 1\8 | 1\6 | |
| Rps2 | | 2\7 | | 3\5 | 8\8 | 3\8 | 5\6 | |
| Rps3a | | 6\6 | 1\8 | 1\6 | 8\8 | 4\4 | 2\2 | |
| Rps3b | | 8\8 | 2\8 | | 1\8 | 6\8 | | |
| Rps3c | 1\8 | 5\7 | 1\8 | 7\8 | 3\8 | 7\7 | 7\8 | |
| Rps4 | | 4\7 | | 8\8 | 4\8 | 6\6 | 6\6 | |
| Rps5 | | 5\6 | 1\8 | | 7\8 | 2\2 | 7\7 | |
| Rps6 | | 3\4 | | 8\8 | 7\8 | 7\8 | 7\8 | |
| Rps7 | 6\7 | 5\6 | 7\7 | 8\8 | 8\8 | 8\8 | 7\7 | |
| Rps8 | | 1\8 | | | 5\8 | 8\8 | 6\8 | |
| Planting Date | Dec. 14, 2005 | Dec. 14, 2005 | Dec. 14, 2005 | Dec. 15, 2005 | Dec. 15, 2005 | Dec. 15, 2005 | Dec. 15, 2005 | |
| Inoculation Date | Dec. 20, 2005 | Dec. 20, 2005 | Dec. 20, 2005 | Dec. 22, 2005 | Dec. 22, 2005 | Dec. 22, 2005 | Dec. 22, 2005 | |
| Data | Dec. 28, 2005 | Dec. 28, 2005 | Dec. 28, 2005 | Dec. 28, 2005 | Dec. 28, 2005 | Dec. 28, 2005 | Dec. 28, 2005 | |

†first number indicates number of plants killed; second number indicates number inoculated.
‡Soybean varieties carrying known Rps genes.
¶ blank cells indicate all plants survived A summary of the traits and characteristics of soybean cultivar HFPR-5 as compared to several competing varieties of commercial and non-commercial soybeans of similar maturity is shown in Tables 3-4.

TABLE 3

Agronomic performance of HFPR-5 in Ohio Trials, 2006 (advanced line test B).

| Name | mat | lodg | ht | sdwt | sdqual | yldwe | yldpc | yldwc | yldnw | yldwo | yld |
|---|---|---|---|---|---|---|---|---|---|---|---|
| Wyandot | 19.2 | 1.4 | 30.8 | 16.0 | 2.1 | 67.9 | 49.0 | 42.9 | 74.4 | 51.3 | 57.1 |
| HS0-3243 | 23.3 | 1.6 | 33.6 | 12.7 | 1.4 | 71.3 | 57.3 | 53.5 | 82.8 | 53.3 | 63.7 |
| Dennison | 23.6 | 1.6 | 34.1 | 14.3 | 1.4 | 78.2 | 54.9 | 44.4 | 80.2 | 58.0 | 63.1 |
| Kottman | 28.2 | 1.4 | 33.1 | 14.5 | 1.3 | 80.9 | 57.2 | 49.3 | 76.8 | 56.0 | 64.0 |
| 93B87 | 28.9 | 1.6 | 34.0 | 15.0 | 1.5 | 79.4 | 66.8 | 57.8 | 84.2 | 59.7 | 69.6 |
| SC 9394RR | 32.7 | 1.8 | 35.1 | 13.2 | 1.3 | 70.1 | 58.2 | 27.9 | 78.3 | 61.9 | 59.3 |
| HFPR-5 | 29.0 | 1.6 | 34.4 | 15.3 | 1.3 | 72.0 | 54.6 | 53.8 | 84.5 | 55.9 | 64.2 |
| Prohio | 32.8 | 2.1 | 38.2 | 14.6 | 1.5 | 76.9 | 61.6 | 52.0 | 72.3 | 60.6 | 64.7 | yldwe = yield (bu/a) at South Charleston, OH;
yldpc = yield (bu/a) at Plain City, OH;
yldwc = yield (bu/a) at Lakeview, OH;
yldnw = yield (bu/a) at Hoytville, OH;
yldwo = yield (bu/a) at Wooster, OH;
yld = mean yield across all locations.

TABLE 4

Performance of HFPR-5 in Ohio Soybean Performance Trials, 2005

| | Entry | | | Yield (bu/a) | | | | | |
|---|---|---|---|---|---|---|---|---|---|
| | mat. rating | Rps genes | partial resistance[a] | North Region | Central Region | South Region | All locations | Protein % | Oil % |
| Sandusky | 2.8 | lk | 4.3 | 47.1 | 40.0 | 55.2 | 47.4 | 38.7 | 22.7 |
| Wyandot | 3.0 | 3a | 3.2[b] | 47.9 | 51.0 | — | — | 39.9 | 21.7 |
| Dilworth | 3.1 | lk + 3a | — | 54.9 | 51.8 | 62.5 | 56.4 | 41.0 | 21.6 |
| Wellman 313 | 3.2 | lk + 3a | — | 62.0 | 53.9 | — | — | 41.4 | 20.8 |

TABLE 4-continued

Performance of HFPR-5 in Ohio Soybean Performance Trials, 2005

| Entry | | | | Yield (bu/a) | | | | | |
|---|---|---|---|---|---|---|---|---|---|
| | mat. rating | Rps genes | partial resistance[a] | North Region | Central Region | South Region | All locations | Protein % | Oil % |
| Ohio GF1 | 3.4 | 3a | 5.8 | 49.0 | 44.4 | 55.2 | 49.5 | 42.0 | 20.2 |
| Resnik | 3.4 | lk | 4.7 | 48.4 | 47.6 | 59.0 | 51.7 | 42.4 | 21.0 |
| Dennison | 3.4 | lk + 3a | — | 58.0 | 54.0 | 67.7 | 59.9 | 40.9 | 21.3 |
| Kottman | 3.7 | lk + 3a | 3.0 | 56.5 | 52.2 | 62.7 | 57.1 | 41.6 | 21.0 |
| HFPR-5 | 3.8 | lk + 3a + 8 | 3.3 | 57.0 | 53.3 | 64.7 | 58.3 | 42.0 | 20.4 |

[a]Response to *P. sojae* rated from 1 (highly resistant) to 9 (highly susceptible) for the partial resistance trait.
[b]Retest gave a value of 5.3.

The HFPR-5 cultivar has shown uniformity and stability, as described in the following variety description information. It has been self-pollinated a sufficient number of generations with careful attention to uniformity of plant type. The line has been increased with continued observation for uniformity.

Soybean cultivar HFPR-5 has the following morphologic and other characteristics (based primarily on data collected at Columbus and Wooster, Ohio).

TABLE 5

Traits for soybean cultivar HFPR-5

| | |
|---|---|
| Roundup-Ready ® | No |
| STS ® | No |
| Flower color | white |
| Pubescence color | Light tawny |
| Mature pod color | Tan |
| hilum color | black |
| plant height | medium |
| seed size | moderate |
| iron chlorosis | moderately susceptible |
| Shattering | resistant |
| purple stain | resistant |
| frogeye leaf spot | susceptible |
| maturity rating | 3.8 |

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed and the present invention, in particular embodiments, also relates to transformed versions of the claimed variety or line.

Plant transformation involves the construction of an expression vector which will function in plant cells. Such a vector comprises DNA comprising a gene under control of, or operatively linked to, a regulatory element (for example, a promoter). The expression vector may contain one or more such operable linked gene/regulatory element combinations. The vector(s) may be in the form of a plasmid and can be used alone or in combination with other plasmids to provide transformed soybean plants using transformation methods as described below to incorporate transgenes into the genetic material of the soybean plant(s).

Expression Vectors for Soybean Transformation: Marker Genes

Expression vectors include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., Proc. Natl. Acad. Sci. USA, 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986)). Other selectable marker genes confer resistance to herbicides such as glyphosate, glufosinate or bromoxynil (Comai et al., Nature 317:741-744 (1985), Gordon-Kamm et al., Plant Cell 2:603-618 (1990) and Stalker et al., Science 242:419-423 (1988)).

Selectable marker genes for plant transformation not of bacterial origin include, for example, mouse dihydrofolate reductase, plant 5-enolpyruvylshikimate-3-phosphate synthase and plant acetolactate synthase (Eichholtz et al., Somatic Cell Mol. Genet. 13:67 (1987), Shah et al., Science 233:478 (1986), Charest et al., Plant Cell Rep. 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., Plant Mol. Biol. Rep. 5:387 (1987), Teeri et al., EMBO J. 8:343 (1989), Koncz et al., Proc. Natl. Acad. Sci. USA 84:131 (1987), DeBlock et al., EMBO J. 3:1681 (1984)).

In vivo methods for visualizing GUS activity that do not require destruction of plant tissue are available (Molecular Probes publication 2908, IMAGENE GREEN, p. 1-4 (1993) and Naleway et al., J. Cell Biol. 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., Science 263: 802 (1994)). GFP and mutants of GFP maybe used as screenable markers.

Expression Vectors for Soybean Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters—An inducible promoter is operably linked to a gene for expression in soybean. Optionally, the inducible promoter is operably linked to a nucleotide sequence encoding a signal sequence which is operably linked to a gene for expression in soybean. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Mett et al., Proc. Natl. Acad. Sci. USA 90:4567-4571 (1993)); In2 gene from maize which responds to benzenesulfonamide herbicide safeners (Hershey et al., Mol. Gen. Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., Proc. Natl. Acad. Sci. USA 88:0421 (1991)).

B. Constitutive Promoters—A constitutive promoter is operably linked to a gene for expression in soybean or the constitutive promoter is operably linked to a nucleotide sequence encoding a signal sequence which is operably linked to a gene for expression in soybean.

Many different constitutive promoters can be utilized in the instant invention. Exemplary constitutive promoters include, but are not limited to, the promoters from plant viruses such as the 35S promoter from CaMV (Odell et al., Nature 313:810-812 (1985)) and the promoters from such genes as rice actin (McElroy et al., Plant Cell 2: 163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, XbaI/NcoI fragment 5' to the Brassica napus ALS3 structural gene (or a nucleotide sequence similarity to said XbaI/NcoI fragment), represents a particularly useful constitutive promoter. See PCT application WO 96/30530.

C. Tissue-specific or Tissue-preferred Promoters—A tissue-specific promoter is operably linked to a gene for expression in soybean. Optionally, the tissue-specific promoter is operably linked to a nucleotide sequence encoding a signal sequence which is operably linked to a gene for expression in soybean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai et al., Science 23:476-482 (1983) and Sengupta-Gopalan et al., Proc. Natl. Acad. Sci. USA 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., Plant Mol. Biol. 20:49 (1992); Close, P. S., Master's Thesis, Iowa State University (1993); Knox, C., et al., Plant Mol. Biol. 9:3-17 (1987); Lerner et al., Plant Physiol. 91:124-129 (1989); Frontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); Steifel, et al., Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to one embodiment, the transgenic plant provided for commercial production of foreign protein is a soybean plant. In another embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. Examples of these methodologies are discussed in Glick and Thompson, Methods in Plant Molecular Biology and Biotechnology, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Examples of genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al. Cell 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., Gene 48:109 (1986), who disclose the cloning and nucleotide sequence of a Bt B-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., Plant Molec. Biol. 24:25 (1994), who disclose the nucleotide sequences of several *Clivia miniata* mannose-binding lectin genes.

E. A vitamin-binding protein such as avidin. See PCT application US 93/06487 which teaches the use of avidin and avidin homologues as larvicides against insect pests.

F. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor 1), Sumitani et al., Biosci. Biotech. Biochem. 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., which discloses genes encoding insect-specific, paralytic neurotoxins.

I. An insect-specific venom produced in nature by a snake, a wasp, etc. For example, see Pang et al., Gene 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hornworm chitinase, and Kawalleck et al., Plant Molec. Biol. 21:673 (1993), who provide the nucleotide sequence of the parsley ubi4-2 polyubiquitin gene.

L,. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol.

104:1467 (1994), who provide the nucleotide sequence of a maize calmodulin cDNA clone.

M. A hydrophobic moment peptide. See PCT application WO 95/16776, which discloses peptide derivatives of tachyplesin which inhibit fungal plant pathogens, and PCT application WO 95/18855 which teaches synthetic antimicrobial peptides that confer disease resistance N. A membrane permease, a channel former or a channel blocker. For example, see the disclosure of Jaynes et al., Plant Sci 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. See Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., Nature 366:469 (1993), who show that transgenic plants expressing recombinant antibody genes are protected from virus attack.

R. A developmental-arrestive protein produced in nature by a pathogen or a parasite. Thus, fungal endo-.alpha.-1,4-D-polygalacturonases facilitate fungal colonization and plant nutrient release by solubilizing plant cell wall homo-.alpha.-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

S. A developmental-arrestive protein produced in nature by a plant. For example, Logemann et al., Bio/Technology 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S., Current Biology, 5(2) (1995).

U. Antifungal genes. See Cornelissen and Melchers, Plant Physiol., 101:709-712 (1993); Parijs et al., Planta 183:258-264 (1991) and Bushnell et al., Can. J. of Plant Path. 20(2): 137-149 (1998).

V. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., Bio/Technology 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., Theor. Appl. Genet. 83:435 (1992).

C. An herbicide that inhibits photosynthesis, such as a triazine (psbA and gs+ genes) and a benzonitrile (nitrilase gene). Przibila et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Natl. Acad. Sci. USA 89:2625 (1992).

B. Decreased phytate content—1) Introduction of a phytase-encoding gene enhances breakdown of phytate, adding more free phosphate to the transformed plant. For example, see Van Hartingsveldt et al., Gene 127:87 (1993), for a disclosure of the nucleotide sequence of an Aspergillus niger phytase gene. 2) A gene could be introduced that reduced phytate content. This could be accomplished by cloning and then reintroducing DNA associated with the single allele which is responsible for maize mutants characterized by low levels of phytic acid. See Raboy et al., Maydica 35:383 (1990).

C. Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus* mutants fructosyltransferase gene), Steinmetz et al., Mol. Gen. Genet. 20:220 (1985) (micleotide sequence of *Bacillus subtilis* levansucrase gene), Pen et al., Bio/Technology 10:292 (1992) (production of transgenic plants that express *Bacillus licheniformis* .alpha.-amylase), Elliot et al., Plant Molec. Biol. 21:515 (1993) (nucleotide sequences of tomato invertase genes), Sogaard et al., J. Biol. Chem. 268:22480 (1993) (site-directed mutagenesis of barley .alpha.-amylase gene), and Fisher et al., Plant Physiol. 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

4. Genes that Control Male Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for Soybean Transformation

Numerous methods for plant transformation have been developed including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc. Boca Raton, 1993) pages 67-88. In addition, expression vectors and in-vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra and Moloney et al., Plant Cell Reports 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation where DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., Part. Sci. Technol. 5:27 (1987); Sanford, J. C., Trends Biotech. 6:299 (1988); Klein et al., Bio/Tech. 6:559-563 (1988); Sanford, J. C. Physiol Plant 7:206 (1990); Klein et al., Biotechnology 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., Bio/Technology 9:996 (1991). Alternatively, liposome and spheroplast fusion have been used to introduce expression vectors into plants. Deshayes et al., EMBO J., 4:2731 (1985); Chiristou et al., Proc Natl. Acad. Sci. USA 84:3962 (1987). Direct uptake of DNA into protoplasts using $CaCl_2$ precipitation, polyvinyl alcohol or poly-L-ornithine have also been reported. Hain et al., Mol. Gen. Genet. 199:161 (1985) and Draper et al., Plant Cell Physiol. 23:451 (1982). Electroporation of protoplasts and whole cells and tissues have also been described (Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994)).

Following transformation of soybean target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular soybean line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Single-Gene Conversions

When the term "soybean plant" is used in the context of the present invention, this also includes any single gene conversions of that variety. The term single gene converted plant as used herein refers to those soybean plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8 or more times to the recurrent parent. The parental soybean plant that contributes the gene for the desired characteristic is termed the nonrecurrent or donor parent. This terminology refers to the fact that the nonrecurrent parent is used one time in the backcross protocol and therefore does not recur. The parental soybean plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic; examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185; 5,973,234 and 5,977,445; the disclosures of which are specifically hereby incorporated by reference. The Rps8 gene is described in U.S. patent application Ser. No. 10/778,018, filed Feb. 12, 2004, to St. Martin et al., the entire contents of which are incorporated by reference.

Tissue Culture

Further reproduction of the variety can occur by tissue culture and regeneration. Tissue culture of various tissues of soybeans and regeneration of plants therefrom is well known and widely published. For example, reference may be had to Komatsuda, T. et al., Crop Sci. 31:333-337 (1991); Stephens, P. A., et al., Theor. Appl. Genet. (1991) 82:633-635; Komatsuda, T. et al., Plant Cell, Tissue and Organ Culture, 28:103-113 (1992); Dhir, S. et al., Plant Cell Reports (1992) 11:285-289; Pandey, P. et al., Japan J. Breed. 42:1-5 (1992); and Shetty, K., et al., Plant Science 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce soybean plants having the physiological and morphological characteristics of soybean cultivar HFPR-5.

As used herein, the term "tissue culture" indicates a composition comprising isolated cells of the same or a different type or a collection of such cells organized into parts of a plant. Examples of types of tissue cultures include, but are not limited to, protoplasts, calli, plant clumps, and plant cells that can generate tissue culture that are intact in plants or parts of plants, such as embryos, pollen, flowers, seeds, pods, leaves, stems, roots, root tips, anthers, pistils and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention is also directed to methods for producing a soybean plant by crossing a first parent soybean plant with a second parent soybean plant wherein the first or second parent soybean plant is a soybean plant of cultivar HFPR-5. Further, both first and second parent soybean plants can come from soybean cultivar HFPR-5. Thus, any such methods using soybean cultivar HFPR-5 are part of this invention: selfing, backcrosses, hybrid production, crosses to populations, and the like. All plants produced using soybean cultivar HFPR-5 as at least one parent are within the scope of this invention, including those developed from cultivars derived from soybean cultivar HFPR-5. For example, this soybean cultivar could be used in crosses with other, different, soybean plants to produce the first generation ($F_1$) soybean hybrid seeds and plants with superior characteristics. The cultivar of the invention can also be used for transformation where exogenous genes are introduced and expressed by the cultivar of the invention. Genetic variants created either through traditional breeding methods using soybean cultivar HFPR-5 or through transformation of cultivar HFPR-5 by any of a number of protocols known to those of skill in the art are intended to be within the scope of this invention.

The following describes breeding methods that may be used with soybean cultivar HFPR-5 in the development of further soybean plants. One such embodiment is a method for developing a cultivar HFPR-5 progeny soybean plant in a soybean plant breeding program comprising: obtaining the soybean plant, or a part thereof, of cultivar HFPR-5, utilizing said plant or plant part as a source of breeding material and selecting a soybean cultivar HFPR-5 progeny plant with molecular markers in common with cultivar HFPR-5 and/or with morphological and/or physiological characteristics selected from the characteristics listed in Table 5. Breeding steps that may be used in the soybean plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of soybean cultivar HFPR-5 progeny soybean plants, comprising crossing cultivar HFPR-5 with another soybean plant, thereby producing a population of soybean plants, which, on average, derive 50% of their alleles from soybean cultivar HFPR-5. A plant of this population may be selected and repeatedly selfed or sibbed with a soybean cultivar resulting from these successive filial generations. One embodiment of this invention is the soybean cultivar produced by this method and that has obtained approximately 50% of its alleles from soybean cultivar HFPR-5.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes soybean cultivar HFPR-5 progeny soybean plants comprising a combination of at least two cultivar HFPR-5 traits selected from the group consisting of those listed herein (e.g. in Table 5), so that said progeny soybean plant is not significantly different for said traits than soybean cultivar HFPR-5 as determined at the 5% significance level when grown in the same environmental conditions. Using techniques described herein, molecular markers may be used to identify said progeny plant as a soybean cultivar HFPR-5 progeny plant. For example, molecular markers for the identification of the Rps8 trait locus, such as those described in U.S. patent application Ser. No. 10/778,018, filed Feb. 12, 2004, can be used to identify a soybean plant carrying Rps8. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of soybean cultivar HFPR-5 may also be characterized through their filial relationship with soybean cultivar HFPR-5, as for example, being within a certain number of breeding crosses of soybean cultivar HFPR-5. A breeding cross is a cross made to introduce new genetics into the progeny, and is distinguished from a cross, such as a self or a sib cross, made to select among existing genetic alleles. The lower the number of breeding crosses in the pedigree, the closer the relationship between soybean cultivar HFPR-5 and its progeny. For example, progeny produced by the methods described herein may be within 1, 2, 3, 4 or 5 breeding crosses of soybean cultivar HFPR-5.

As used herein, the term "plant" includes plant cells, plant protoplasts, plant cell tissue cultures from which soybean plants can be regenerated, plant calli, plant clumps, and plant cells that are intact in plants or parts of plants, such as embryos, pollen, ovules, flowers, pods, leaves, roots, root tips, anthers, cotyledons, hypocotyls, stems, pistils, and the like.

INDUSTRIAL USES

The seed of soybean cultivar HFPR-5, the plant produced from the seed, the hybrid soybean plant produced from the crossing of the variety with any other soybean plant, hybrid seed, and various parts of the hybrid soybean plant can be utilized for human food, livestock feed, and as a raw material in industry.

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board and American Soybean Association Special Report 92S, May 1990).

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthier, less expensive replacement for animal protein in meats as well as in dairy-type products.

DEPOSIT INFORMATION

A deposit of the proprietary soybean cultivar designated HFPR-5 disclosed above and recited in the appended claims has been made with the American Type Culture Collection (ATCC), 10801 University Boulevard. Manassas, Va. 20110. The date of deposit was Aug. 17, 2007. The deposit is intended to meet all of the requirements of 37 C.F.R. 1.801-1.809. The ATCC accession number is PTA-8606. The deposit will be maintained in the depository for a period of 30 years, or 5 years after the last request, or for the effective life of the patent, whichever is longer, and will be replaced as necessary during that period.

The present invention should not be considered limited to the specific examples described above, but rather should be understood to cover all aspects of the invention. Various modifications, equivalent processes, as well as numerous structures and devices to which the present invention may be applicable will be readily apparent to those of skill in the art.

What is claimed is:

1. A soybean seed designated HFPR-5, a sample of said seed deposited under ATCC Accession No. PTA-8606.

2. A plant, or parts thereof, having all of the physiological and morphological characteristics of a soybean plant produced by growing soybean seed designated HFPR-5, a sample of said seed deposited under ATCC Accession No. PTA-8606.

3. The plant of claim 2, wherein the plant is produced by growing soybean seed designated HFPR-5, a sample of said seed deposited under ATCC Accession No. PTA-8606.

4. The plant of claim 2, wherein the plant is regenerated from tissue culture of regenerable cells of an HFPR-5 soybean plant, or parts thereof, wherein the HFPR-5 soybean plant is produced by growing soybean seed designated HFPR-5, a sample of said seed deposited under ATCC Accession No. PTA-8606.

5. The plant part of claim 2, wherein the plant part is selected from the group consisting of: leaf, pollen, stomatal cell, embryo, meristematic cell, root, root tip, anther, flower, ovule, seed, stem, pod, petal, cotyledons, hypocotyl, pistils and cells thereof.

6. A tissue culture of regenerable cells of a soybean plant, or parts thereof, wherein the soybean plant is produced by growing soybean seed designated HFPR-5, a sample of said seed deposited under ATCC Accession No. PTA-8606.

7. The tissue culture according to claim 6, wherein the cells are obtained from a plant part selected from the group consisting of: leaf, pollen, stomatal cell, embryo, meristematic cell, root, root tip, anther, flower, ovule, seed, stem, pod, petal, cotyledons, hypocotyl, pistils and cells thereof.

8. The tissue culture of claim 6, wherein a soybean plant regenerated from the tissue culture has all of the morphological and physiological characteristics of an HFPR-5 soybean plant, or parts thereof, wherein the HFPR-5 soybean plant is produced by growing soybean seed designated HFPR-5, a sample of said seed deposited under ATCC Accession No. PTA-8606.

9. A method for producing a progeny soybean plant or seed, comprising: crossing a first parent soybean plant with a second parent soybean plant to produce the progeny soybean plant or seed, wherein the first parent soybean plant is produced by growing soybean seed designated HFPR-5, a sample of said seed deposited under ATCC Accession No. PTA-8606.

10. The method of claim 9, wherein the first parent soybean plant is different from the second parent soybean plant and the method produces a hybrid progeny soybean plant or seed.

11. The method of claim 9, wherein the progeny soybean plant or seed has all of the physiological and morphological characteristics of a soybean plant produced by growing soybean seed designated HFPR-5, a sample of said seed deposited under ATCC Accession No. PTA-8606.

12. The method of claim 9, wherein the second parent soybean plant is transgenic.

13. The method of claim 12 wherein the transgenic second parent soybean plant contains genetic material conferring a trait selected from the group consisting of herbicide resistance, nematode resistance, insect resistance, resistance to disease, male sterility, and a combination thereof.

14. The method of claim 13 wherein the resistance to disease is through an oxalate oxidase encoding polynucleotide sequence or an oxalate decarboxylase encoding polynucleotide sequence.

15. A progeny soybean plant or seed produced by crossing a first parent soybean plant with a second parent soybean plant, wherein the first parent soybean plant is produced by growing soybean seed designated HFPR-5, a sample of said seed deposited under ATCC Accession No. PTA-8606.

16. The progeny soybean plant or seed of claim 15, wherein the first parent soybean plant is different from the second parent soybean plant and the resultant progeny soybean plant or seed is a hybrid.

17. The progeny soybean plant or seed of claim 15, wherein the progeny soybean plant or seed has all of the physiological and morphological characteristics of a soybean plant produced by growing soybean seed designated HFPR-5, a sample of said seed deposited under ATCC Accession No. PTA-8606.

18. The progeny soybean plant or seed of claim 15, wherein the second parent soybean plant is transgenic.

19. The progeny soybean plant or seed of claim 18, wherein the transgenic second parent soybean plant contains genetic material conferring a trait selected from the group consisting of herbicide resistance, nematode resistance, insect resistance, resistance to disease, male sterility, and a combination thereof.

20. The progeny soybean plant or seed of claim 19, wherein the resistance to disease is through an oxalate oxidase encoding polynucleotide sequence or an oxalate decarboxylase encoding polynucleotide sequence.

21. A method of introducing a desired trait into soybean cultivar HFPR-5 wherein the method comprises:
  i. crossing a HFPR-5 plant, produced by growing soybean designated HFPR-5, a sample of said seed deposited under ATCC Accession No. PTA-8606, with a plant of another soybean cultivar that comprises one or more desired traits to produce progeny plants wherein the desired trait is selected from the group consisting of male sterility, herbicide resistance, insect resistance, modified fatty acid metabolism, modified carbohydrate metabolism, decreased phytate content, resistance to bacterial disease, resistance to fungal disease and resistance to viral disease;
  ii. selecting one or more progeny plants that have the one or more desired traits to produce selected progeny plants;
  iii. crossing the selected progeny plants with the HFPR-5 plants to produce backcross progeny plants;
  iv. selecting for backcross progeny plants that have the one or more desired traits and all of the physiological and morphological characteristics of soybean cultivar HFPR-5 listed in Table 5; and
  v. repeating steps (iii) and (iv) three or more times in succession to produce selected fourth or higher backcross progeny plants that comprise the one or more desired traits and all of the physiological and morphological characteristics of soybean cultivar HFPR-5 listed in Table 5.

22. The method of claim 21, wherein the desired trait is herbicide resistance and the resistance is conferred to an herbicide selected from the group consisting of imidazolinone, sulfonylurea, glyphosate, glufosinate, L,-phosphinothricin, triazine and benzonitrile.

23. The method of claim 21, wherein the desired trait is insect resistance and the insect resistance is conferred by a transgene encoding a *Bacillus thuringiensis* endotoxin.

24. The method of claim 21, wherein the one or more desired traits are modified fatty acid metabolism, modified carbohydrate metabolism, or decreased phytate content, and said desired trait is conferred by a nucleic acid encoding a protein selected from the group consisting of phytase, fructosyltransferase, levansucrase, α-amylase, invertase and starch branching enzyme or transforming a plant with an antisense gene of stearyl-ACP desaturase.

25. A plant produced by the method of claim 21.

* * * * *